United States Patent [19]

Fischell

[11] Patent Number: 6,074,371

[45] Date of Patent: Jun. 13, 2000

[54] BLUNT INJECTION NEEDLE FOR A PEN-TYPE INJECTOR

[75] Inventor: Robert E. Fischell, Dayton, Md.

[73] Assignee: Magnolia Medical, LLC, Dayton, Md.

[21] Appl. No.: 09/150,908

[22] Filed: Sep. 10, 1998

[51] Int. Cl.[7] ................................................ A61M 5/00
[52] U.S. Cl. ........................................................ 604/207
[58] Field of Search ................................... 604/207, 181, 604/187, 264, 48

[56] References Cited

U.S. PATENT DOCUMENTS

| | | | |
|---|---|---|---|
| 4,710,180 | 12/1987 | Johnson | 604/274 |
| 4,869,717 | 9/1989 | Adair | 604/51 |
| 4,973,318 | 11/1990 | Holm et al. | 604/208 |
| 5,342,316 | 8/1994 | Wallace | 604/167 |
| 5,462,535 | 10/1995 | Bonnichsen et al. | 604/272 |
| 5,531,810 | 7/1996 | Fullemann | 96/105 |
| 5,536,249 | 7/1996 | Castellano et al. | 604/65 |
| 5,599,323 | 2/1997 | Bonnichsen et al. | 604/272 |
| 5,759,178 | 6/1998 | Wells | 604/240 |

OTHER PUBLICATIONS

The power of the Homolin Pen from the Eli Lilly, Co., Winter/Spring 1999.

*Primary Examiner*—Wynn Wood Coggins
*Assistant Examiner*—Deborah Blyveis

[57] ABSTRACT

Disclosed is a needle assembly to be used with a pen-type injector and a percutaneously placed catheter device for intravenous infusion or a subcutaneously inserted cannula that is part of an injection set. Unlike all prior art needle assemblies which have a sharp point at the needle's distal end, the needle assembly described herein has a blunt tip so as to avoid any inadvertent needle sticks. This invention envisions using such a blunt tipped needle assembly connected to a pen-type injector and used with an injection set that has a cannula placed in the subcutaneous tissue. This invention also envisions using such a blunt tipped needle assembly with a pen-type injector for intravenous injections of medication through any intravenous catheter that has a septum through which the blunt needle of the pen-type injector can be placed.

6 Claims, 2 Drawing Sheets

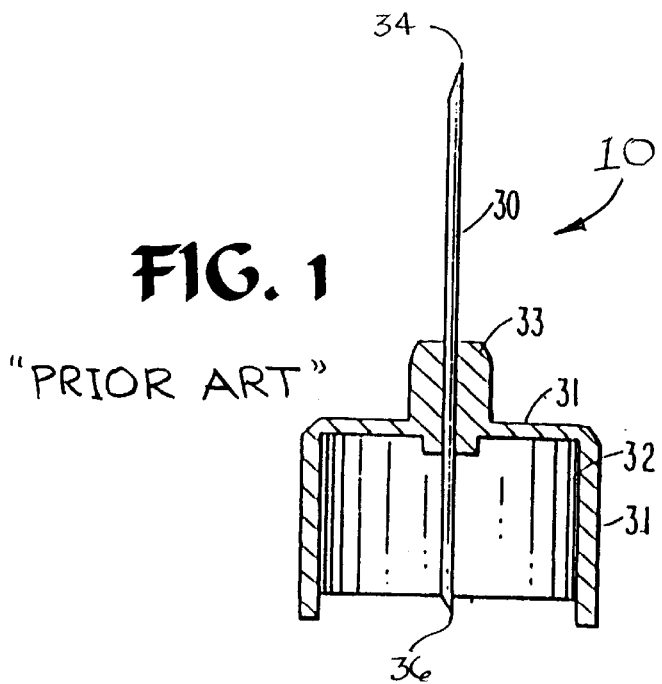
FIG. 1 "PRIOR ART"
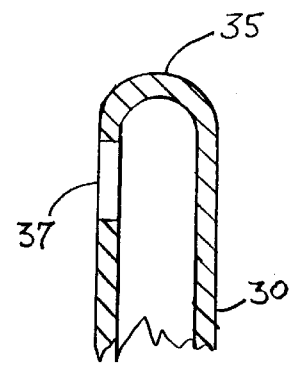
FIG. 3
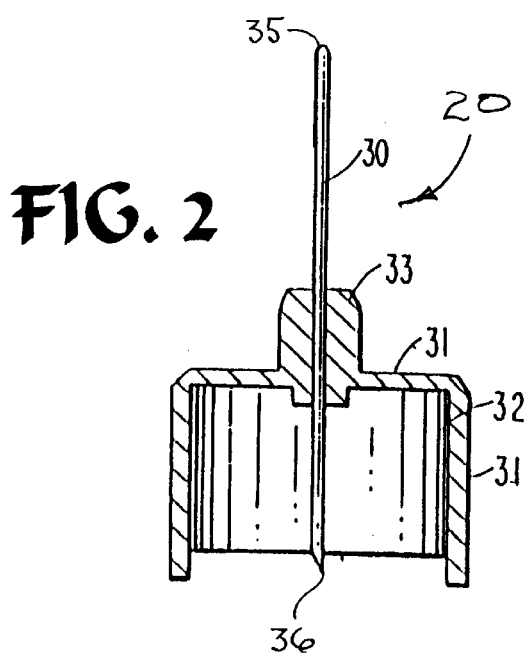
FIG. 2
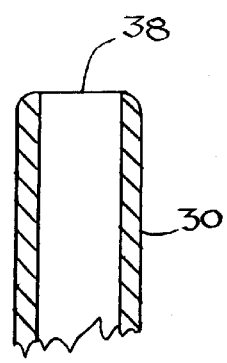
FIG. 4

BLUNT INJECTION NEEDLE FOR A PEN-TYPE INJECTOR

FIELD OF USE

This invention is in the field of devices that prevent inadvertent needle sticks when a health care worker injects a medication into a patient.

BACKGROUND OF THE INVENTION

In the U.S.A. in 1997 there were approximately 800,000 inadvertent needle sticks to health care workers that resulted in approximately 2,000 cases of hepatitis C and 35 cases of HIV infection. Inadvertent needle sticks could be avoided if blunt tip injection needles were used to deliver medication to the patients. However, such injections would be very painful to the patients unless they were placed through a percutaneously placed catheter device such as an injection set that uses a subcutaneous cannula as described in U.S. patent application Ser. No. 09/110,360 entitled, "DEVICE FOR SUBCUTANEOUS INJECTION". Although that patent application describes an appropriate injection set, it only describes the use of blunt needles attached to a hypodermic syringe and does not describe the use of a pen-type injector having a blunt needle attached for administering medication to a patient.

In U.S. Pat. Nos. 5,599,323 and 5,728,074 two different types of pen-type injectors are described in detail. These pen-type injectors are now in use throughout the world as an improved means for delivering a preset dosage of medication. However, all such pen-type injectors use removable needles that have sharp points that can cause inadvertent needle sticks to the health care worker that uses them in a hospital or nursing home situation.

SUMMARY OF THE INVENTION

The present invention is a needle assembly to be used with a pen-type injector and a percutaneously placed catheter device for intravenous infusion or a subcutaneously inserted cannula that is part of an injection set. Unlike all prior art needle assemblies which have a sharp point at the needle's distal end, the needle assembly described herein has a blunt tip so as to avoid any inadvertent needle sticks. This invention envisions using such a blunt tipped needle assembly connected to a pen-type injector and used with an injection set that has a cannula placed in the subcutaneous tissue. This invention also envisions using such a blunt tipped needle assembly with a pen-type injector for intravenous injections of medication through any intravenous catheter that has a septum through which the blunt needle of the pen-type injector can be placed.

Thus it is an object of this invention to provide a needle assembly for a pen-type injector that can provide either subcutaneous or intravenous injections using a blunt tipped needle assembly.

Another object of this invention is to provide a blunt tipped needle assembly that is designed to enter either a subcutaneous injection set or certain types of intravenous catheters.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 1 is a longitudinal cross section of a prior art needle assembly that uses a needle having a sharp point at its distal end.

FIG. 2 is a longitudinal cross section of a needle assembly that uses a blunt tipped needle.

FIG. 3 is a highly enlarged longitudinal cross section of a distal portion of a blunt tipped needle.

FIG. 4 is a highly enlarged longitudinal cross section of a distal portion of a blunt tipped needle of an alternative design.

DETAILED DESCRIPTION OF THE DRAWINGS

Figure 5:
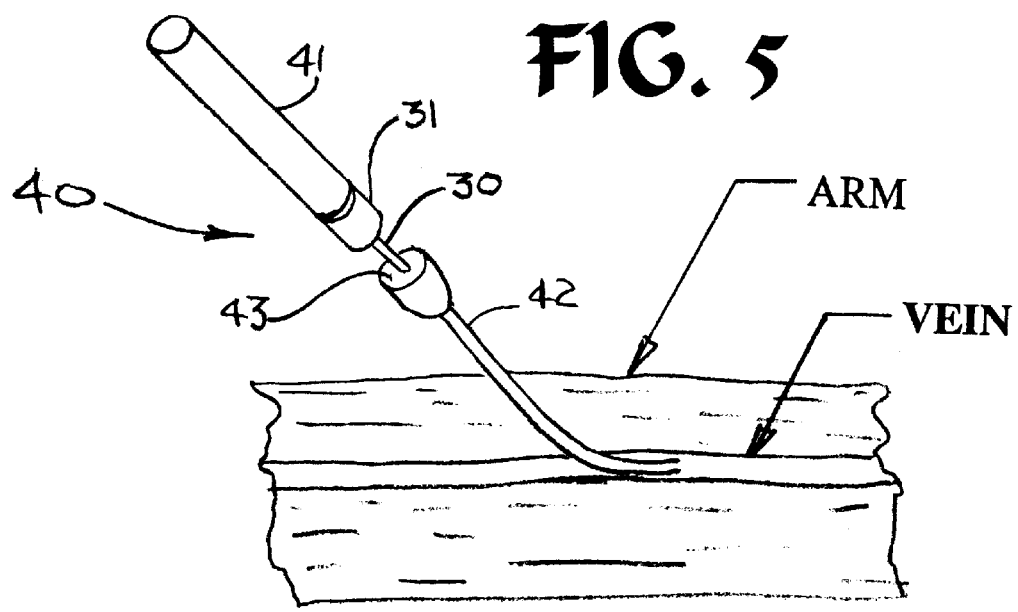
FIG. 5 illustrates the configuration of a pen-type injector with a blunt tipped needle placed through a septum that is part of an intravenous catheter that is placed in a vein.

FIG. 1 is a prior art needle assembly 10 for a pen-type injector that has an embedded needle shaft 30, and a hub 31 having a central protrusion 33 and internal threads 32 to attach the needle assembly 10 to a pen-type injector (not shown). The needle shaft 30 has a sharp distal end point 34 for penetrating the skin and a sharp point 36 at its proximal end for penetrating a medication cartridge that would be situated in the pen-type injector.

FIG. 2 shows a needle assembly 20 having the same design for the needle shaft 30, the hub 31, threads 32, protrusion 33 and sharp proximal end point 36. However, the novel feature of the needle assembly 20 is that there is a blunt point 35 at the distal end of the needle shaft 30.

FIG. 3 shows a blunt tip 35 on the needle shaft 30 that has a side opening 37. FIG. 4 shows an alternative embodiment of a blunt tip design that has a rounded end of the needle shaft 30 with a end hole 38. The designs shown in either FIG. 3 or FIG. 4 (or any other type of blunt tip design) could be used with the needle assembly 20.

The needle assembly 20 could be used with any type of pen-type injector. Examples of such pen-type injectors are shown in U.S. Pat. No. 5,599,323 and U.S. Pat. No. 5,728,074. The needle assembly 20 can be used with various types of percutaneously placed catheter device such as some intravenous catheter systems or an injection set as described in the U.S. patent application Ser. No. 09/110,360 which is included herein by reference. Any such percutaneously placed catheter device would use a septum in order to prevent infection from entering the bloodstream or the subcutaneous tissue. The blunt tip 35 (or 38) would be of a small enough diameter to pass through such a septum in order to deliver medication from the pen-type injector. Typically, the needle shaft 30 would have a diameter of less than 1.0 mm so that the blunt tip 35 could readily pass through such a septum.

FIG. 5 illustrates an intravenous injection system 40 having a pen-type injector 41 that has a hub 31 into which is embedded a needle shaft 30 that has a blunt tip at its distal end. The needle shaft 30 passes through the septum 43 of an intravenous catheter 42 that is shown with its distal end placed into a vein in an arm.

Figure 6:
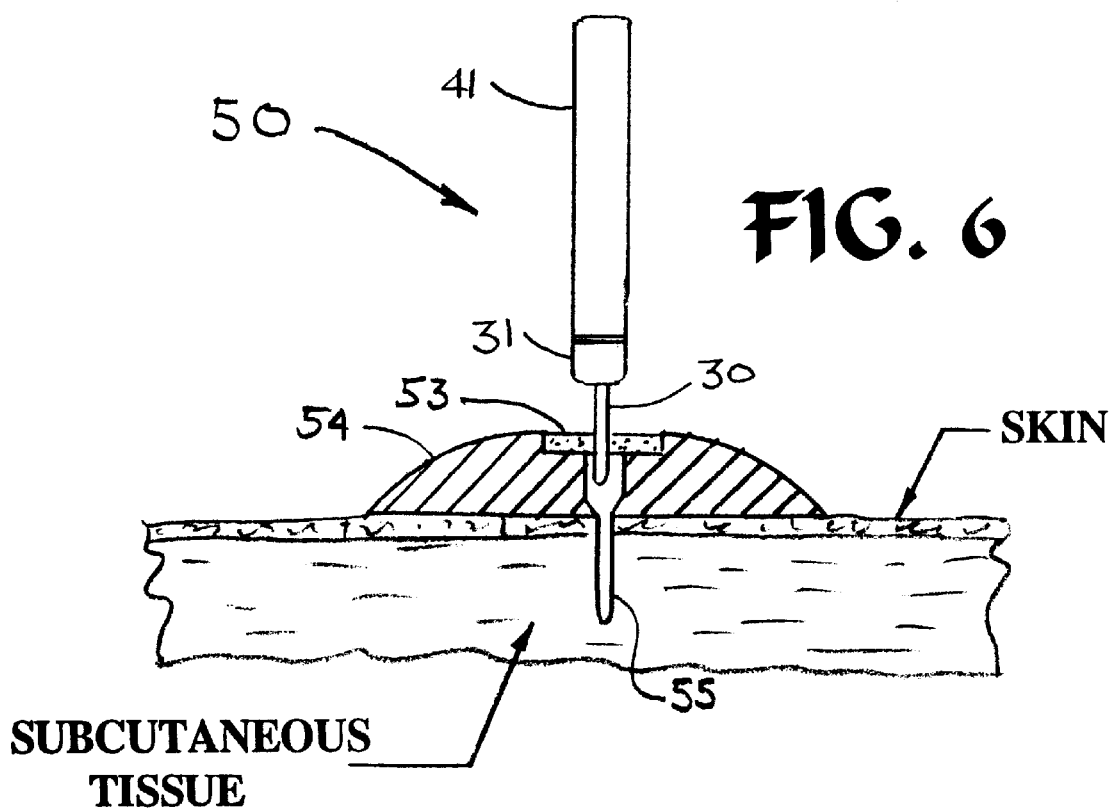
FIG. 6 illustrates the configuration of a pen-type injector with a blunt-tipped needle placed through the septum of an injection set that has a cannula placed for subcutaneous infusion of medication.

FIG. 6 illustrates a subcutaneous injection system 50 having a pen-type injector 41 that has a hub 31 and a needle shaft 30 that is placed through the septum 53 of an injection set 54. The injection set 54 has a short cannula 55 with a distal opening that is placed into subcutaneous tissue.

The pen-type injector 41 (with needle hub 31 and needle shaft 30) as shown in FIGS. 5 and 6 is well known in the art of insulin delivery systems and is described in detail in many articles and patents including the previously cited U.S. Pat. No. 5,728,074. Pen-type injectors are all characterized as being elongated, generally cylindrical structures having a numerical indicator that can be set to deliver a preset quantity of medication that is less than the total quantity of medication contained within the pen-type injector. This preset quantity of medication from the pen-type injector is delivered by a single completed stroke of a plunger.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A system for preventing inadvertent needle sticks when administering medication to a patient, the system comprising:

a needle assembly having a hub and a needle shaft embedded into the hub, the needle shaft having a distal end and a proximal end and having a blunt tip at the needle shaft's distal end;

a pen-type injector adapted for attachment of the needle assembly, the pen-type injector having an elongated, generally cylindrical shape, a total quantity of medication contained therein, a numerical indicator means for setting a preset quantity of medication and a plunger for delivering in a single completed stroke that preset quantity of medication into the patient, the preset quantity of medication being less than the total quantity of medication contained within the pen-type injector; and, an injection system adapted for percutaneous placement through the patient's skin, the injection system having a septum through which the blunt tip at the distal end of the needle shaft can be placed to deliver medication from the pen-type injector into the patient.

2. The system of claim 1 wherein there is a sharp point at the proximal end of the needle shaft.

3. The system of claim 1 wherein the injection system is an injection set having a cannula placed for the subcutaneous injection of medication.

4. The system of claim 1 wherein the injection system is an intravenous catheter adapted for the infusion of medication into a vein.

5. The system of claim 1 wherein the needle shaft has a side hole through which the medication is delivered.

6. The system of claim 1 wherein the needle shaft has an end hole through which the medication is delivered.

* * * * *